United States Patent [19]

Daly

[11] 4,230,896

[45] Oct. 28, 1980

[54] CATALYTIC STEAM DEALKYLATION OF ALKYL PHENOLS

[75] Inventor: Francis P. Daly, Lawrenceville, N.J.

[73] Assignee: Hydrocarbon Research, Inc., Lawrenceville, N.J.

[21] Appl. No.: 964,814

[22] Filed: Nov. 30, 1978

[51] Int. Cl.$^3$ ............................................. C07C 37/50
[52] U.S. Cl. ............................................. 568/805
[58] Field of Search ............................. 568/805, 806

[56] References Cited

U.S. PATENT DOCUMENTS

| | | | |
|---|---|---|---|
| 2,366,497 | 1/1945 | Dawson | 568/806 |
| 2,386,969 | 10/1945 | Mattox | 260/672 |
| 2,435,038 | 1/1948 | Gilbert et al. | 260/621 |
| 2,692,293 | 10/1954 | Heinemann | 260/672 |
| 2,734,929 | 2/1956 | Doumani | 260/672 |
| 2,746,996 | 5/1956 | Neuworth | 260/621 |
| 2,773,917 | 12/1956 | Coonradt et al. | 260/672 |
| 2,998,457 | 8/1961 | Paulson | 568/805 |
| 3,071,627 | 1/1963 | Mackay et al. | 260/621 |
| 3,091,646 | 5/1963 | Leston | 568/805 |
| 3,296,316 | 4/1969 | Neuworth | 260/621 |
| 3,436,434 | 3/1972 | Lester | 260/672 |
| 3,649,707 | 4/1972 | Lester | 260/672 |
| 3,686,340 | 8/1972 | Partick et al. | 260/672 R |
| 3,751,505 | 8/1973 | Bergomi | 260/672 R |
| 3,760,023 | 9/1973 | Partick et al. | 260/672 R |
| 4,008,181 | 2/1977 | Dorawala et al. | 568/805 |

FOREIGN PATENT DOCUMENTS

| | | | |
|---|---|---|---|
| 38-21720 | 3/1963 | Japan | 568/805 |
| 399498 | 4/1974 | U.S.S.R. | 568/805 |

OTHER PUBLICATIONS

Chemical Abstracts 55; 22240g.
Chemical Abstract 71; 123, 263 m.
Rabinovich et al., Dealkylation of Toluene on Metals of the Platinum group in the presence of Steam.
Grenoble "Amer. Chem. Soc. Meeting Mar. 20–23, 1977 New Orlean Kenetics of Steam Dealkylation of Toluene over Group VII Noble Metal."
Grenoble, "Journal of Catalysis," vol. 51, pp. 212–220 (1978).
Grenoble, "Journal of Catalysis," vol. 51, pp. 203–211 (1978).

*Primary Examiner*—Werren B. Lone
*Attorney, Agent, or Firm*—Michael A. Jacobs

[57] ABSTRACT

This invention provides a method for the selective dealkylation of alkylated phenols, which method comprises reacting a feed solution comprising a mixture of alkylated phenols with steam in the presence of a catalyst comprising a hydrous carrier, at least one catalyst deactivation suppressor, and at least one promoter. A salt of an alkali metal may be added to the feed to enhance the selectivity of phenol in the product.

11 Claims, 1 Drawing Figure

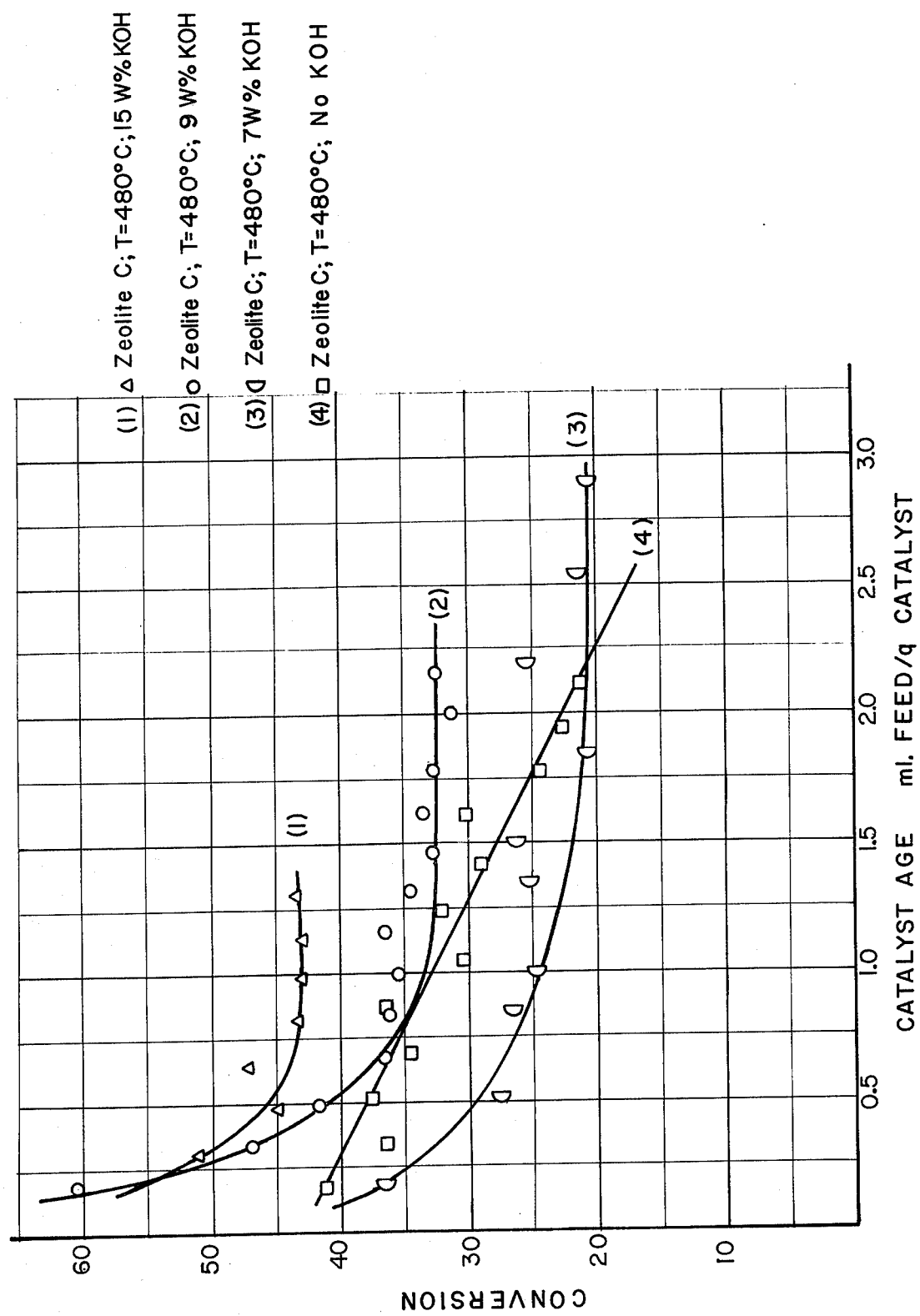

CATALYTIC STEAM DEALKYLATION OF ALKYL PHENOLS

BACKGROUND OF THE INVENTION

1. Field of the Invention

This invention relates to a method for the selective dealkylation of alkyl phenols. More particularly, this invention is directed to a catalytic dealkylation process whereby alkyl phenols are reacted with steam in the presence of a catalyst to yield phenol.

2. Description of the Prior Art

Phenol has a wide range of industrial uses, for example, in the production of nylon, plywood, molding compounds, foundry resins, herbicides, surfactants and the like. More particularly, the greatest use for phenol is in the formation of phenolic resins which are primarily consumed in the production of plywood, laminates, and insulation.

The major process for the preparation of phenol involves air oxidation of cumene to yield a hydroperoxide. This hydroperoxide is then subjected to a mild acid treatment to yield phenol and acetone. This process accounts for about 93% of the synthetic production of phenol.

Processes for the dealkylation of alkyl aromatics have acquired significant importance in the petroleum and petrochemical industries. More particularly, these processes have been extensively used in supplementing the benzene demand by dealkylating readily available alkyl substituted benzenes. It is well established that alkyl aromatics, such as toluene, can be dealkylated to lighter aromatics, such as benzene, by reacting such alkyl aromatics with hydrogen in the presence or absence of a catalyst at an elevated pressure and temperature for a controlled length of time. The result of such conditions is the removal of the alkyl group which combines with the hydrogen to yield saturated aliphatic hydrocarbons.

Such hydrodealkylation conditions have been applied to alkyl phenols. However, it has been found that under these conditions, not only the alkyl substituents are removed, the hydroxyl group is also cleaved from the aromatic ring and replaced by hydrogen, thus forming benzene which is undesirable. The cleaved hydroxyl group also combines with the hydrogen to form water. Consequently, alkyl phenols, when subjected to hydrodealkylation conditions, yield, in addition to water, alkyl aromatics and benzene instead of phenol. Furthermore, in excessive amount of hydrogen is consumed.

As a result of the energy crisis, it is becoming increasingly apparent that the cost of hydrogen production from once non-expensive hydrocarbon feedstocks is rapidly increasing. It follows that the cost of hydrogen consuming processes, such as hydrodealkylation, also increases significantly. Thus, interest in processes using steam in place of hydrogen for reforming petroleum feedstocks is increasing. Steam is also preferred because it is readily available and yields, on reaction, readily recoverable and valuable hydrogen. Furthermore, catalytic steam processes are preferable because the presence of the catalyst lowers the energy of activation of the reaction, and, therefore, requires less severe reaction conditions.

The catalytic steam dealkylation of toluene and other benzene homologues has been extensively patented and reported in the literature. Typical catalyst compositions include zeolites or amorphous inorganic oxides, such as silica, alumina, silica-alumina, and the like, in conjunction with other metals or metal oxides. These types of catalysts have shown remarkable initial activity when compared to non-catalytic processes under the same conditions. For the steam dealkylation of toluene over gamma-alumina supported noble metals, benzene selectivity in the range of from 60 to about 98 mole % has been reported. Unfortunately, this type of catalyst undergoes rapid deactivation which appears to be due to the formation of coke on the surface of the catalyst, thus rendering the catalytic surface relatively inaccessible to further reaction. As time elapses, the activity of the catalyst declines to such a low level that the process must be temporarily halted to regenerate or replace the catalyst. As a result, the deactivation of the catalyst makes the catalytic steam dealkylation process only marginally effective as a commercial process.

Thus, it is apparent that there is a need for a process for dealkylating alkyl phenols, such process being capable of commercial application as well as economically feasible.

It has been found by the present invention that the alkyl group in an alkylated phenol may be removed by reacting the alkylated phenol with steam in the presence of a catalyst which comprises a hydrous carrier, a deactivation suppressor, and a promoter.

It has also been discovered that by mixing the alkylated phenol feed with an alkali metal salt, the rate of catalyst deactivation is reduced and also the selectivity for phenol is enhanced.

SUMMARY OF THE INVENTION

According to the present invention, alkyl phenols may be dealkylated by reacting the phenols with steam in the presence of a catalyst comprising a hydrous carrier or support, a catalyst deactivation suppressor which is one or more of Group I-A and Group II-A metal oxides, and a promoter such as a Group VIII metal and Group VI-B metal oxides.

To further reduce the rate of catalyst deactivation and also enhance the selectivity of phenol in the above reaction, one or more of alkali metal salts may be dissolved in the phenol feed, with the feed then reacted with steam in the presence of a catalyst.

By using the present invention, the selectivity for phenol in the dealkylation reaction may be as high as approximately 95%.

DESCRIPTION OF THE DRAWING

FIG. 1 is a graph showing the relationship between catalyst deactivation and catalyst age for different catalysts.

DETAILED DESCRIPTION OF THE INVENTION

The present invention is directed to a process for the catalytic steam dealkylation of alkyl phenols to phenol. By the term "dealkylation," as used herein, is meant an operation in which alkyl groups containing 1–4 carbon atoms are split off from an alkylated phenol without removing the hydroxyl group, i.e. the alkyl group is removed whereas the hydroxyl group remains attached to the benzene ring.

According to the present process, a feed solution containing a mixture of alkyl phenols is reacted with steam. As indicated above, the feed solution comprises one or more alkyl phenols having one or more alkyl substituents, each containing from one to four carbon atoms. The alkyl chain in the substituents may either be straight or branched. Useful examples of alkyl phenols include the isomers of cresol, xylenol, ethylphenol, n-propylphenol, and the like. Although the dealkylation reaction of this invention may be applied to a single alkylated phenol, it is preferred to use a feed which comprises a plurality of substituted phenols wherein the alkyl groups have different chain lengths. Typical examples of feed solutions include tar acids derived from coke oven tars, coal-derived liquids, and the like.

The other reactant in the dealkylation reaction of this invention is steam. The steam may be unsaturated, saturated, or superheated, with superheated steam being preferred.

As to the catalyst which is useful in the present process, this generally comprises the following components: a hydrous carrier, a catalyst deactivation suppressant, and a promoter. The catalyst carrier may be a clay, a silica, a metal oxide a zeolite and the like. Preferred porous carriers include alumina, silica, silica-alumina, silica-magnesia, silica-titania, silica-berrilia, silica-zirconia, and the like. Among these, alumina, more specifically gamma alumina, and zeolite are specially preferred. It is of significance to note that the carrier must be hydrous since the water absorbed on the carrier is believed to be the source of hydrogen for the dealkylation reaction.

As to the catalyst deactivation suppressant, Group I-A and Group II-A metal oxides are useful to reduce the rate of deactivation of the catalyst due to coke formation on the catalyst surface. Useful Group I-A metals include lithium, sodium, potassium, rubidium, and cesium, with potassium being preferred. Useful Group II-A metals include magnesium, calcium, strontium and barium. Among the above-listed metal oxides, potassium and barium oxides are preferred.

As to the promoter, it may be a Group VIII metal or a Group VI-B oxide. Useful Group VIII metals include iron, cobalt, nickel, ruthenium, rhodium, palladium, osmium, iridium, and platinum. Examples of useful Group VI-B metals include chromium, molybdenum, and tungsten. In the preferred embodiment, the promoter comprises a mixture of palladium and chromium oxide ($Cr_2O_3$).

In accordance with the present invention, the catalyst comprises from about 0.1 to about 10% by weight, preferably from about 1 to about 5% by weight, based on the total weight of the catalyst, of the deactivation suppressant and from about 0.1 to about 20% by weight, preferably from about 0.3 to about 5% by weight, based on the total weight of the catalyst, of the promoter, the balance being the carrier.

The dealkylation reaction according to the present invention may be carried out continuously in a fixed bed or fluidized bed reactor. The molar ratio of steam to alkyl phenols may range from about 1:1 to about 15:1, with about 1:1 to about 10:1 being preferred. As to the reaction temperature, this may range from about 250° to about 700° C., although from about 250° to about 550° C. is preferred. The reaction may be carried out at a pressure ranging from about 1 to 50 atmospheres, with from about 1 to about 10 atmospheres being preferred. The rate at which the alkyl phenols may be passed over the bed of catalyst (weight hourly space velocity) ranges from about 0.1 to about 5.0 grams of phenol/hr/gram of catalyst, with from about 0.5 to 1.5 gram phenol/hr/gram of catalyst being preferred.

In another embodiment of the present invention, it has been found that the rate of catalyst deactivation may be reduced and the selectivity for the phenol improved substantially by dissolving an alkali metal salt in the feed. The salt may be present in the range of from about 0.1 to about 20% by weight, preferably from about 5 to about 18% by weight, based on the total weight of the phenol feed and steam. Examples of alkali metals include lithium, sodium, potassium, rubidium, and cesium, with potassium being preferred. As to the salts, examples thereof include chloride, hydroxides, carbonates, and sulfates, with hydroxide being preferred. Among the above-mentioned alkali metal salts, potassium hydroxide is preferred. The alkyl phenol feed, after having the alkali metal salt added thereto, may be reacted with steam in the presence of a catalyst in accordance with the present invention as described hereinabove.

Although the mechanism for the present invention is not clearly understood, the following is given as an explanation thereof. In the dehydroxylation of alkyl phenols, water is formed as a product. Therefore, when water is added to the reaction mixture as a reactant, the equilibrium is shifted against dehydroxylation. This reduction in the dehydroxylation reaction is believed to lead to an increase in the dealkylation reaction. In addition, it is believed that the steam, which is passed simultaneously with the alkyl phenol feedstock over the catalyst bed, supplies the hydrogen necessary for the dealkylation when adsorbed on the carrier of the catalyst. The present inventor believes that it is these two functions of the steam which lead to the desirable results obtained in the instant invention. However, it must be noted that the above mechanisms are offered merely as an explanation and the present inventor does not wish to be bound thereto.

The following examples are given to illustrate the process of the present invention. It should be noted that these examples are intended to be only illustrative and should not be construed as limiting the scope of this invention.

EXAMPLE 1

Various packed beds of catalysts having the compositions shown in Table 2 were heated in a nitrogen atmosphere for about one hour at the operating temperature prior to the introduction of steam and the feedstock containing the alkyl phenols. The feedstock had composition as shown in Table 1 below.

TABLE 1

| Feed Composition, W % | Example 1 | Example 2 |
|---|---|---|
| o-cresol | 0 | 27.6 |
| m, p-cresol | 96.0 | 58.0 |
| o-ethylphenol | 0.8 | 0.6 |
| xylenols | 3.2 | 13.8 |

The feedstock and steam were then passed over the heated catalyst bed. The weight hourly space velocity was about 1 gram feedstock/hr/gram catalyst. A steam to feedstock molar ratio of about 6 was maintained, with the operating pressure being at about 1 atmosphere. The organic liquid product was collected in a chilled receiver and analyzed by gas chromatography. The experimental conditions and results are shown in Table 2. The level of conversion is based on the total mole percent of products formed, namely, phenol, benzene, toluene, and xylene. The phenol selectivity is the weight percent of phenol formed with respect to the sum of the weights of the products: phenol, benzene, toluene, and xylene.

TABLE 2

| Catalyst | Temperature °C. | Cat. Age, ml feed/ gm. cat | Conversion Mole % | Phenol Selectivity W % |
|---|---|---|---|---|
| 1% Pt/γ-Al$_2$O$_3$ | 450 (842° F.) | 0.50 | 33.54 | 87.85 |
| 1% Pd/γ-Al$_2$O$_3$ | 450 | 0.53 | 38.22 | 86.50 |
| 0.3% Pd + 0.3% Cr$_2$O$_3$/ γ-Al$_2$O$_3$ | 450 | 0.50 | 34.79 | 92.59 |
| 2.3% K + 1% Pd/ γ-Al$_2$O$_3$ | 450 | 0.50 | 36.00 | 94.29 |
| Zeolite | 480 (896° F.) | 0.50 | 34.19 | 74.92 |
| 2% Ba + Zeolite | 480 | 0.99 | 35.11 | 81.81 |

EXAMPLE 2

In this example, the procedure outlined in Example 1 was repeated, with exception that the feedstock, as described in Table 1, was mixed with potassium hydroxide prior to reaction. The experimental conditions and results for substantially the same catalyst age are summarized in Table 3.

TABLE 3

| Catalyst | Temperature °C. | W % KOH | Cat. Age, ml feed/ gm. cat. | Conversion Mole % | Phenol Selectivity W % |
|---|---|---|---|---|---|
| Zeolite | 480 (896° F.) | 15 | 1.14 | 42.93 | 74.34 |
| Zeolite | 480 | 9 | 1.16 | 36.36 | 84.09 |
| Zeolite | 480 | 7 | 1.35 | 25.18 | 87.46 |
| Zeolite | 480 | 0 | 1.24 | 32.04 | 68.49 |

From the above description, it is apparent that the instant invention provides a process for dealkylation of alkyl phenols wherein the deactivation of the catalyst is decreased while the selectivity for phenol is increased. This improvement in catalyst activity vs catalyst age for various amounts of potassium hydroxide in the feed is further shown by FIG. 1. It is seen that by adding between about 5 and 18% potassium hydroxide (KOH) to the feed, the catalyst deactivation first declines and then levels off with increasing catalyst age (curves 1, 2, 3) whereas with no potassium hydroxide in the feed the catalyst activity continues to decline (curve 4). Furthermore, the molar percent conversion of the alkyl phenol feedstock with steam to phenol is greater when the increased amounts of potassium hydroxide salt is added to the feed.

What is claimed is:

1. A process of dealkylating alkyl phenol to form a phenol product comprising reacting a feed solution comprising a mixture of alkyl phenols with steam in the presence of a catalyst, the catalyst comprising a hydrous carrier, from about 0.1 to about 10% by weight of at least one catalyst deactivation suppressor selected from the group consisting of Group I-A and Group II-A metals, and from about 0.1 to about 20% by weight of at least one promoter selected from the group consisting of Group VIII metals and Group VI-B metal oxides, the mole ratio of steam to alkyl phenols being from about 1:1 to about 15:1, the reaction being carried out at a temperature of from about 250° to about 700° C. and at a pressure of from about 1 to about 50 atmospheres, the weight hourly space velocity of the alkyl phenols is from about 0.1 to about 5.0 gm phenol/hr/gram catalyst.

2. The process of claim 1 wherein the feed solution comprises one or more alkyl phenols from the group consisting of the isomers of cresol, xylenol, ethylphenol, n-propylphenol, and the like, with steam.

3. The process of claim 1 wherein the hydrous carrier is a member of the group consisting of clay, silica, metal oxide, and zeolite.

4. The process of claim 1 wherein the feed solution comprises m, p-cresol, o-ethylphenol, and various isomers of xylenol, the hydrous carrier is selected from the group consisting of alumina, silica, silica-alumina, silica magnesia, and zeolite, the catalyst deactivation suppressor is selected from the group consisting of potassium and barium and is present in an amount of from about 1 to about 5% by weight, the promoter is selected from the group consisting of platinum, palladium, and chromium oxide (Cr$_2$O$_3$) and is present in an amount of from about 0.3 to about 5% by weight, the reaction being carried out at a temperature of from about 250° to about 550° C. and a pressure of from about 1 to about 10 atmospheres, the mole ratio of feed to steam being about 1 to 10, and the weight hourly space velocity being about 0.5 to 1.5 gm phenols/hr/gm catalyst.

5. The process of claim 1 wherein the feed solution comprises about 96.0 W % m, p-cresol, 0.8 W % o-ethylphenol, and 3.2 W % various isomers of xylenol, the hydrous carrier is selected from the group consisting of alumina, silica-alumina, and zeolite, the catalyst deactivation suppressor is selected from the group consisting of potassium and barium and is present in an amount of from about 1 to about 5% by weight, the promoter is selected from the group consisting of platinum, palladium, and chromium oxide (Cr$_2$O$_3$) and is present in an amount of from about 0.3 to about 5% by weight, the reaction being carried out at a temperature of from about 450° to about 480° C. and a pressure of from about 1 to about 2 atmospheres, the mole ratio of feed to steam being about 6, and the weight hourly space velocity being about 1 gm phenols/hr/gm catalyst.

6. A process of dealkylating alkyl phenol to form a phenol product comprising reacting a feed solution comprising from about 0.1 to about 18% by weight of an alkali metal salt and a mixture of alkyl phenols with steam in the presence of a catalyst, the catalyst comprising a hydrous carrier, from about 0.1 to about 10% by weight of at least one catalyst deactivation suppressor selected from the group consisting of Group I-A and Group II-A metals, and from about 0.1 to about 20% by weight of at least one promoter selected from the group consisting of Group VIII metals and Group VI-B metal oxides, the mole ratio of steam to alkyl phenols being from about 1:1 to about 15:1, the reaction being carried out at a temperature of from about 250° to about 700° C. and at a pressure of from about 1 to about 50 atmospheres, the weight hourly space velocity being from about 0.1 to about 5.0 gm phenol/hr/gram catalyst.

7. The process of claim 6 wherein the feed solution comprises from about 0.1 to about 18% by weight of the alkali metal salt and one or more alkyl phenols from the group consisting of the isomers of cresol, xylenol, ethylphenol, n-propylphenol, and the like with steam.

8. The process of claim 6 wherein the hydrous carrier is a member of the group consisting of clay, silica, metal oxide, and zeolite.

9. The process of claim 6 wherein the alkali metal salt in the feed solution is potassium hydroxide.

10. The process of claim 6 wherein the feed solution comprises from about 5 to about 18% by weight of potassium hydroxide, a mixture of alkyl phenols consisting of o-cresol, m, p-cresol, o-ethylphenol, and various isomers of xylenol, the hydrous carrier is selected from the group consisting of alumina, silica, silica-magnesia, silica titania, and zeolite, the promoter is selected from the group consisting of platinum, palladium, and chromium oxide ($Cr_2O_3$), and is present in an amount of about 0.3 to 5% by weight based on the weight of the catalyst, the reaction being carried out at a temperature of from about 250° to about 550° C. at a pressure of from about 1 to about 10 atmospheres, the mole ratio of feed to steam being about 1 to 10 and the weight hourly space velocity being about 0.5 to 1.5 gram phenol/hr/gram catalyst.

11. The process of claim 6 wherein the feed solution comprises from about 7 to about 15% by weight of potassium hydroxide, a mixture of alkyl phenols consisting of o-cresol, (27.6 W %), m, p-cresol (58.0 W %), o-ethylphenol (0.6 W %), and various isomers of xylenol (13.8 W %), the hydrous carrier is selected from the group consisting of alumina and zeolite, the promoter is palladium, and is present in an amount of about 1% by weight based on the weight of the catalyst, the reaction being carried out at a temperature of from about 450° to about 480° C. at a pressure of from about 1 to about 2 atmospheres, the mole ratio of feed to steam being about 6, and the weight hourly space velocity being about 1 gram phenol/hr/gram catalyst.

* * * * *